United States Patent
Welch

(10) Patent No.: US 11,744,788 B2
(45) Date of Patent: Sep. 5, 2023

(54) METHOD OF ENCOURAGING GROWTH AND REGROWTH OF HAIR IN HUMAN MALES TECHNICAL AREA

(71) Applicant: James D. Welch, Omaha, NE (US)

(72) Inventor: James D. Welch, Omaha, NE (US)

( * ) Notice: Subject to any disclaimer, the term of this patent is extended or adjusted under 35 U.S.C. 154(b) by 0 days.

(21) Appl. No.: 17/803,532

(22) Filed: Aug. 15, 2022

(65) Prior Publication Data

US 2023/0061150 A1   Mar. 2, 2023

Related U.S. Application Data

(60) Provisional application No. 63/360,760, filed on Oct. 27, 2021.

(51) Int. Cl.
| | |
|---|---|
| *A61K 8/49* | (2006.01) |
| *A61Q 7/00* | (2006.01) |
| *A61K 8/92* | (2006.01) |
| *A61N 2/02* | (2006.01) |
| *A61P 17/14* | (2006.01) |

(52) U.S. Cl.
CPC ............ *A61K 8/4953* (2013.01); *A61K 8/922* (2013.01); *A61N 2/02* (2013.01); *A61P 17/14* (2018.01); *A61Q 7/00* (2013.01); *A61H 2205/021* (2013.01)

(58) Field of Classification Search
None
See application file for complete search history.

(56) References Cited

U.S. PATENT DOCUMENTS

| | | | |
|---|---|---|---|
| 8,088,123 B2* | 1/2012 | Kinoshita et al. | |
| 8,192,473 B2* | 6/2012 | Tucker et al. | |
| 8,609,072 B2* | 12/2013 | Florence et al. | |
| 8,834,940 B2* | 9/2014 | Trigiante | |
| 8,877,762 B2* | 11/2014 | Hu et al. | |
| 8,927,554 B2* | 1/2015 | Hu et al. | |
| 9,006,291 B2* | 4/2015 | Brinkenhoff | |
| 9,125,936 B2* | 9/2015 | Meyer et al. | |
| 9,408,795 B2* | 8/2016 | Duggan et al. | |
| 9,532,941 B2* | 1/2017 | Shapiro et al. | |
| 9,956,156 B2* | 5/2018 | Wu | |
| 9,962,360 B2* | 5/2018 | Miller et al. | |
| 9,962,444 B2* | 5/2018 | Malek | |
| 10,420,962 B2* | 9/2019 | Holmes | |
| 10,456,344 B2* | 10/2019 | Bhogal et al. | |
| 10,688,030 B2* | 1/2020 | Nakano et al. | |
| 10,561,593 B2* | 2/2020 | Wu | |
| 10,688,037 B1* | 6/2020 | Morley et al. | |
| 10,925,824 B2* | 2/2021 | Wu | |
| 11,000,466 B2* | 5/2021 | Wu | |
| 11,033,473 B2* | 6/2021 | Okunishi et al. | |
| 11,039,996 B2* | 6/2021 | Wu | |
| 11,052,059 B2* | 7/2021 | Schmidt | |
| 11,110,272 B2* | 9/2021 | Ingman et al. | |
| 11,116,770 B2* | 9/2021 | Sinclair | |
| 2009/0258085 A1* | 10/2009 | Bach | A61P 17/00 424/600 |
| 2011/0087310 A1* | 4/2011 | Chen et al. | |
| 2012/0065708 A1* | 3/2012 | Kinoshita et al. | |
| 2013/0041432 A1* | 2/2013 | Tucker et al. | |

OTHER PUBLICATIONS

Strange biological actuator nourishes aging hair follicles, renourish email materials.*

\* cited by examiner

*Primary Examiner* — Nannette Holloman
(74) *Attorney, Agent, or Firm* — James D. Welch

(57) ABSTRACT

Methodology for encouraging hair growth in male humans, and more particularly to methodology which involves application of electromagnetic radiation, mechanical vibrations, along with applications of combined minoxidil, mint oil, (preferably menthol containing essential peppermint oil), ginger oil, lavender oil, castor bean oil, jojoba oil; melaleuca oil, cumin oil, D-alpha tocopherol (vitamin E) infused oil, biotin infused oil and a single selection, or dry mixture and/or liquid "tea" formed from selections from the group consisting of powdered saw palmetto; powdered horsetail; powdered ginger; powdered stinging nettles; powdered horny goat weed; powdered pueraria lobate; powdered *Tribulus terrestris*; powdered ashwagandha; powdered capsicum; powdered habenero; powdered green tea; powdered sage; powdered gingko biloba; powdered myrrh; powdered alpha-hydroxy; powdered *Aloe vera*; powdered wheat protein; powdered wheat starch; powdered casein, powdered keratin, powdered folic acid; powdered fenugreek seed and powdered biotin powdered ginseng Root; powdered vetiver grass; powdered caffeine; powdered Co-enzyme Q; powdered folate; powdered gotukola leaf; powdered milk thistle; powdered African pygeum; powdered stinging nettles; powdered gingko biloba; powdered myrrh; powdered alpha-hydroxy; powdered caffeine; powdered niacinamide (NAD) and/or niacin; and powdered *Nigella sativa*; powdered *Eclipta alba*; powdered *Centella asiatica*; powdered *Phyllanthus emblica* in water and alcohol, or an oil.

20 Claims, No Drawings

METHOD OF ENCOURAGING GROWTH AND REGROWTH OF HAIR IN HUMAN MALES TECHNICAL AREA

TECHNICAL AREA

The present invention relates to methodology for encouraging hair growth in male humans, and more particularly to methodology for causing regrowth of hair therein involving electromagnetic radiation, along with an application of combined minoxidil, with at least one selection from: mint oil, (preferably menthol containing essential peppermint oil), ginger oil, lavender oil castor bean oil, cumin oil, D-alpha tocopherol (vitamin E) infused oil, biotin infused oil and a single selection, or mixture of selections from the group consisting of dry powdered and/or a "tea" made by the steeping in water (or an oil) of saw palmetto, powdered horsetail; powdered fenugreek seed, powdered horny goat weed; powdered pueraria lobate; powdered *Tribulus terrestris*; powdered ashwagandha; powdered capsicum; powdered habenero; powdered green tea; powdered sage; powdered ginger; powdered vetiver grass; powdered caffeine; powdered Co-enzyme Q; powdered folate; powdered gotukola leaf; powdered milk thistle; powdered African pygeum; powdered stinging nettles; powdered gingko biloba; powdered myrrh; powdered alpha-hydroxy; powdered *Aloe vera*; powdered wheat protein; powdered wheat starch; powdered casein, powdered keratin, powdered folic acid; powdered fenugreek seed and powdered biotin powdered ginseng Root; powdered niacinamide (NAD) and/or niacin; powdered *Nigella sativa*; powdered *Eclipta alba*; powdered *Centella asiatica*; powdered *Phyllanthus emblica*; powdered turmeric; powdered curcumin and powdered pine bark.

BACKGROUND

During the isolation of the Pandemic the Inventor herein, having a researcher's nature and having experienced typical male hair loss over the years, turned his attention to various approaches and materials applicable to achieving hair regrowth.

It is documented that Hair loss in Humans Males well known, and probably equally well resented by most of those afflicted, which includes, as mentioned, the Inventor herein. Decades ago he noticed a thinning of his hair, and adopted use of Minoxidil. That seemed to slow the hair loss, but did not stop it. A few years ago he bought one of the helmets with about 120 sources (LEDs/Lasers) of electromagnetic radiation (650 nm wavelength, 5 mw's each) present therein. Use thereof did lead to some noticeable hair regrowth rather quickly. Recently he added application of Castor oil and essential Peppermint oil to the Minoxidil, and noticed added benefit. Very recently he added applying a single choice or a mixture of selections from the group consisting of powdered saw palmetto; powdered horsetail; powdered fenugreek seed; powdered horny goat weed; powdered pueraria lobate; powdered *Tribulus terrestris*; powdered ashwagandha; powdered capsicum; powdered habenero; powdered green tea; powdered sage; powdered ginger; powdered stinging nettles; powdered gingko biloba; powdered myrrh; powdered alpha-hydroxy; powdered *Aloe vera*; powdered wheat protein; powdered wheat starch; casein; powdered keratin, powdered folic acid and powdered biotin, powdered stinging nettles; powdered *Eclipta alba*; powdered *Centella asiatica*; powdered *Phyllanthus emblica* etc.; are present in substantially equal, or exactly equal amounts by weight, and yet again noticed an improvement.

Most recently, upon realizing that the procedure involving application of electromagnetic radiation and the various topical liquids and powdered materials was not particularly successful in re-growing hair on the frontal portion of his scalp, he has adopted application of vibrations from a hand held vibrator to said frontal scalp areas and generally to the frontal and rearward portions of his scalp. Again, this procedure on its own, is not unknown.

Known relevant patents and Published application that describe application of electromagnetic radiation and various oils and powdered materials to hair challenged areas of a male human scalp are include U.S. Pat. Nos. 9,125,936l; 10,688,030; 11,033,473; 8,088,123; 8,192,473; 2011/0087310; 2012/0065708 and 2013/0041432; U.S. Pat. Nos. 11,039,996; 11,052,059; 11,000,466; 11,110,272; 10,925,824; 11,116,770; 10,688,030; 10,688,032; 10,456,344; 10,561,593; 10,420,962, 8,609,072; 9,956,156; 9,962,444; 9,962,360; 9,408,7951 9,532,941; 9,125,936; 8,877,762; 8,877,762; 9,006,291; 8,927,554 and 8,834,940. Further a simple Ebay Search for Hair Regrowth Caps and Helmets will turn-up many commercially available products.

It is mentioned in particular that Minoxidil has been shown to encourager hair growth in human males. Not so well known, but known, is that peppermint oil, ginger oil and lavender oil etc. also encourages such. And it is further known that castor bean oil encourages human hair growth.

The present invention is not found in a specific step, but rather is found in practicing a combination of steps involving application of electromagnetic radiation and substances known to encourage human male hair growth, in a manner that combines benefits of each.

Even in view of the extensive literature in the area, need remains for easy to practice methodology, practice of which encourages hair growth, and/or regrowth in human males.

DISCLOSURE OF THE INVENTION

The restoration of hair in human males, in the inventor's experience, must be divided into two parts. First, what works on the rearward portion of the upper human male scalp, and second, what works on the forward portion thereof.

Rearward Portion of Scalp

The present invention is a sequence of steps that apply existing sources of electromagnetic radiation, along with minoxidil, mint oil (preferably menthol containing essential peppermint oil), castor bean oil and an additional known single substance, or mixtures of known substances selected from a group consisting of: powdered saw palmetto; powdered horsetail; powdered fenugreek seed; powdered horny goat weed; powdered pueraria lobate; powdered *Tribulus terrestris*; powdered ashwagandha; powdered capsicum; powdered habenero; powdered green tea; powdered sage; powdered ginger; powdered stinging nettles; powdered gingko biloba; powdered myrrh; powdered alpha-hydroxy; powdered *Aloe vera*; powdered wheat protein; powdered wheat starch; powdered casein; powdered keratin, powdered folic acid and powdered biotin powdered zinc; powdered ginseng root; powdered niacinamide (NAD) and/or niacin and powdered *Nigella sativa* powdered *Eclipta alba*; powdered *Centella asiatica*; and powdered *Phyllanthus emblica*.

Where more than one selection is made, a mixture of said powdered selections can be arrived at by providing, by weight, substantially equal amounts of each selection, exact percentages of said powdered selections being limited only in that they sum to 100% in total. Further, said single selection or a mixture of said selections is considered as a unit on par with the minoxidil, peppermint oil and castor bean oil on a volume basis. This can be appreciated by considering that a single application might be comprised of a half a teaspoon of each of the minoxidil, mint oil, cumin oil and castor oil, cumin oil, D-alpha tocopherol (vitamin E) infused oil, biotin infused oil as well as a similar amount of a single selection, or mixture of more than one selection from the above list of powdered selections. It is noted that the half teaspoon measure, or a bit less, is appropriate as a single usage dosage for evident typical male pattern baldness.

The present invention has been arrived at empirically by the inventor over a period of many years by trial and evaluation of results achieved, and has benefitted him. The results of practicing the invention methodology by the inventor, has improved his hair growth over said period of many years, especially in the rearward areas of his scalp.

The present invention can be recited as a method of encouraging hair growth in male humans, comprising the steps of:

in either order practicing steps a) and b):
- a) providing a human scalp comprising at least one hair challenged area in need of hair regrowth;
- b) providing a multiple electromagnetic radiation source containing helmet or cap suitable for placement adjacent to at least said at least one hair challenged area of said human scalp, a vibrator for producing vibrations and liquid sources of minoxidil, mint oil from a substantially or exactly 100% source thereof; ginger oil from a substantially or exactly 100% source thereof; lavender oil from a substantially or exactly 100% source thereof; castor bean oil from a substantially or exactly 100% source thereof; jojoba oil from a substantially or exactly 100% source thereof; melaleuca oil from a substantially pure if not per se. 100% pure source thereof; cumin oil from a substantially or exactly 100% source thereof; D-alpha tocopherol (vitamin E) infused oil; and biotin infused oil.

The method proceeds with, in either order, practicing steps c) and d):
- c) applying electromagnetic radiation provided by said multiple electromagnetic radiation source containing helmet or cap for at least 5 minutes to said at least one hair challenged area while at least one of the multiple electromagnetic radiation sources are energized;
- d) applying to said at least one hair challenged area, and leaving it in place, a volume of liquid comprising at least one selection from the group consisting of:
  - minoxidil solution from a 5% source;
  - mint oil from a substantially or exactly 100% source thereof;
  - ginger oil from a substantially or exactly 100% source thereof;
  - lavender oil from a substantially or exactly 100% source thereof;
  - castor bean oil from a substantially or exactly 100% source thereof;
  - jojoba oil from a substantially or exactly 100% source thereof;
  - melaleuca oil from a substantially pure if not per se. 100% pure source thereof;
  - cumin oil from a substantially or exactly 100% source thereof;
  - D-alpha tocopherol (vitamin E) infused oil; and
  - biotin infused oil;

exact amounts of each selection being limited only in that they sum to 100% by volume in total.

The method can further involve, at some point after steps b) use of the vibrator to apply vibrations to the at least one hair challenged area.

Preferably said method is repeated on a daily basis for a period of years. In the inventor's experience, it is disclosed, that the methodology disclosed herein cannot be expected to provide immediate results on a time scale of days, but rather over a period of years.

Said method can further involve that step d) mint oil comprises at least 1% liquid menthol by volume, such as essential peppermint oil, which is preferred.

Said method can further involve that the step d) components of minoxidil, mint oil; ginger oil; lavender; castor bean oil; jojoba oil; melaleuca oil; cumin oil; D-alpha tocopherol (vitamin E) infused oil; and biotin infused oil components are present in substantially equal, or exactly equal amounts by volume.

The method can also involve, including in the step d) at least an equal amount by volume, at least one selection from the consisting of:
- powdered saw palmetto;
- powdered horsetail;
- powdered fenugreek seed;
- powdered horny goat weed;
- powdered pueraria lobate;
- powdered *Tribulus terrestris*;
- powdered ashwagandha;
- powdered capsicum;
- powdered habenero;
- powdered green tea;
- powdered sage;
- powdered ginger;
- powdered stinging nettles;
- powdered gingko biloba;
- powdered myrrh;
- powdered alpha-hydroxy;
- powdered *Aloe vera*;
- powdered wheat protein;
- powdered wheat starch;
- powdered casein;
- powdered keratin;
- powdered folic acid;
- powdered biotin;
- powdered zinc;
- powdered ginseng Root;
- powdered vetiver grass;
- powdered caffeine;
- powdered Co-enzyme Q;
- powdered folate;
- powdered gotukola leaf;
- powdered milk thistle;
- powdered African pygeum;
- powdered niacinamide (NAD) and/or niacin;
- powdered *Nigella sativa*;
- powdered *Eclipta alba*;
- powdered *Centella asiatica*;
- powdered *Phyllanthus emblica*;
- powdered turmeric;
- powdered curcumin; and
- powdered pine bark;

wherein, when more than one selection is made a mixture of said selections is arrived at by providing, by weight, approximately equal amounts of each selection. Exact percentages of said powdered selections being limited only in that they sum to 100% in total, said single selection or a mixture of said selections is considered as a unit on par with the minoxidil etc. Preferably equal weights of each powdered selection should determine the amount of each, but for the purposes of this invention equal weights can be approximated by providing about half a teaspoon of each selection.

It is clarified that one can make selections from the step d) selection group of powders (when included) then measure out weights of each selected powder and mix the volumes of said selections. A volume thereof is added to the volumes of each of the minoxidil, mint and castor oil from step c) volumes is then sequestered from the mixture of powders. A preferred, but not exclusive, practice is to make volumes of the various components approximately equal.

The step d) components, and when present one or more selections from the group of powdered saw palmetto; powdered horsetail; powdered fenugreek seed; powdered horny goat weed; powdered pueraria lobate; powdered *Tribulus terrestris*; powdered ashwagandha; powdered capsicum; powdered habenero; powdered green tea; powdered sage; powdered ginger; powdered stinging nettles; powdered gingko biloba; powdered myrrh; powdered alpha-hydroxy; powdered *Aloe vera*; powdered wheat protein; powdered wheat starch; powdered casein; powdered keratin, powdered folic acid and powdered biotin powdered stinging nettles; powdered *Eclipta alba*; powdered *Centella asiatica*; powdered *Phyllanthus emblica* in total, can be present in substantially equal, or exactly equal amounts by volume. For instance, each of the minoxidil, mint oil, ginger oil, lavender oil, cumin oil and castor oil; jojoba oil; melaleuca oil; cumin oil; D-alpha tocopherol (vitamin E) infused oil; and biotin infused oil and a unit of the single selection, or a mixture of more than one selection from the list of powdered materials as a unit, can all be of a volume equivalent of a half tea spoon, for application to an area of a human male scalp typical in male pattern baldness. Where a volume greater than appropriate for application to a hair challenged area of a human male scalp is prepared, a volume of the combined components appropriate for application, (eg. two teaspoons in the case of early male pattern baldness) can be sequestered in each individual application.

Said method can involve that at least one of the multiple electromagnetic radiation sources provide a wavelength of 650 nm, (although benefits can be achieved using between about 600 and 1000 nm) at least, and in which step c) is practiced for a time selected from the group consisting of:
  at least 0.5 hours;
  at least 1.0 hours;
  at least 1.5 hours; and
  at least 2.0 hours.
(Note, during the pandemic the inventor has, on a daily basis when time allowed, routinely applied a helmet containing about 120 Laser/LED's that provide electromagnetic radiation of a 650 nm wavelength at 5 mw (other wavelengths and wattages are possible and should be considered as included in the Claims) to his scalp for 1.5 hours or longer at a time, which seemed to be very beneficial).

The method can involve that, with or without practice of step c) more than once, that any of the variants of the step d) mixture is applied to the at least one hair challenged area at least twice a day.

Further, said method can involve, prior to step a) shampooing scalp and any hair present, and while wet providing and applying approximately equal amounts of minoxidil from a 5% solution thereof, and essential peppermint oil, ginger oil, lavender oil, cumin oil and castor oil from 100% sources thereof; and when the shampooed scalp and any hair present is substantially dry, providing and applying at least 1% by volume at least one selection from the group consisting of:
  powdered saw palmetto;
  powdered horsetail;
  powdered fenugreek seed;
  powdered horny goat weed;
  powdered pueraria lobate;
  powdered *Tribulus terrestris*;
  powdered ashwagandha;
  powdered capsicum;
  powdered habenero;
  powdered green tea;
  powdered sage;
  powdered ginger;
  powdered stinging nettles;
  powdered gingko biloba;
  powdered myrrh;
  powdered alpha-hydroxy;
  powdered *Aloe vera;*
  powdered wheat protein;
  powdered wheat starch;
  powdered casein;
  powdered keratin;
  powdered folic acid;
  powdered biotin;
  powdered zinc;
  powdered ginseng Root;
  powdered vetiver grass;
  powdered caffeine;
  powdered Co-enzyme Q;
  powdered folate;
  powdered gotukola leaf;
  powdered milk thistle;
  powdered African pygeum;
  powdered niacinamide (NAD) and/or niacin;
  powdered *Nigella sativa;*
  powdered *Eclipta alba;*
  powdered *Centella asiatica;*
  powdered *Phyllanthus emblica;*
  powdered turmeric;
  powdered curcumin; and
  powdered pine bark;
wherein when more than one selection is made a mixture of said selections is arrived at by providing, by weight, approximately equal amounts of each selection exact percentages of said powdered selections being limited only in that they sum to 100% in total; followed by styling any hair and leaving all materials applied in place.

Further, the method can comprise a step e) that involves providing access to substantially pure or pure per se., one or more selections from the group consisting of:
  powdered saw palmetto;
  powdered horsetail;
  powdered fenugreek seed;
  powdered horny goat weed;
  powdered pueraria lobate;
  powdered *Tribulus terrestris;*
  powdered ashwagandha;
  powdered capsicum;
  powdered habenero;
  powdered green tea;
  powdered sage;
  powdered ginger;
  powdered stinging nettles;
  powdered gingko biloba;
  powdered myrrh;
  powdered alpha-hydroxy;
  powdered *Aloe vera;*
  powdered wheat protein;

powdered wheat starch;
powdered casein;
powdered keratin;
powdered folic acid;
powdered biotin;
powdered zinc;
powdered ginseng Root;
powdered vetiver grass;
powdered caffeine;
powdered Co-enzyme Q;
powdered folate;
powdered gotukola leaf;
powdered milk thistle;
powdered African pygeum;
powdered niacinamide (NAD) and/or niacin;
powdered *Nigella sativa;*
powdered *Eclipta alba;*
powdered *Centella asiatica;*
powdered *Phyllanthus emblica;*
powdered turmeric;
powdered curcumin; and
powdered pine bark;

after step d) applying to said hair challenged area after the liquid in step d) has substantially dried said single selected powder or mixture of selected powders to said at least one region of hair challenged scalp and leaving it in place.

(Note, when applied to dry hair, powdered Keratin alone, or in mixture with other selections, can adhere to hair giving it a fuller appearance. A product from a Company named "Finally Hair Corp." markets a product for just that purpose, which is represented as containing selections from the group of keratin, *Gossyplum herbaceum* and polymers).

Said method can further comprise:

practicing steps f) and g) in either order:
  f) applying electromagnetic radiation provided by a multiple electromagnetic radiation source containing helmet or cap for at least 5 minutes to said at least one hair challenged area while at least one of the multiple electromagnetic radiation sources are energized;
  g) applying to said at least one hair challenged area, and leaving it in place, a liquid comprising at least one selection from the group consisting of:
    minoxidil solution from a 5% source;
    mint oil from a substantially pure if not per se. 100% pure source thereof;
    ginger oil from a substantially pure if not per se. 100% pure source thereof;
    lavender oil from a substantially or exactly 100% source thereof;
    castor bean oil from a substantially pure if not per se. 100% pure source thereof;
    jojoba from a substantially or exactly 100% source thereof oil;
    melaleuca oil from a substantially pure if not per se. 100% pure source thereof;
    cumin oil from a substantially pure if not per se. 100% pure source thereof;
    D-alpha tocopherol (vitamin E) infused oil; and
    biotin infused oil;
exact amounts of each selection being limited only in that they sum to 100% in total by volume.

It is desirable that the step e) powdered selection(s) be left in place so that they remain when steps f) and g) are practiced. For instance, steps f) and g) can be practiced before retiring to bed at night, whereas step e) had been practiced earlier in the day. A morning shampooing is advisable however, to remove the oils, followed by a morning application of at least minoxidil and mint oil.

In the step g) mint oil can comprise at least 1.0-40% liquid menthol by volume, including essential menthol containing peppermint oil.

Said method can involve the components in step g) are present in substantially equal, or exactly equal amounts by volume Said method can involve at least one of the multiple electromagnetic radiation sources provide a wavelength of 650 nm at 5 mw's, and step g) is practiced for a time selected from the group consisting of:
  at least 0.5 hours;
  at least 1.0 hours;
  at least 1.5 hours; and
  at least 2.0 hours.

(Note, at the beginning of practicing the present invention methodology a procedure might involve selecting 2.0 hours during the first three months, 1.5 hours during the second three months, 1.0 hour during the third three months and 0.5 hours in the fourth three months and perhaps even a shorter period thereafter).

Said method can provide that the step d) selections further include a volume of liquid comprising a "tea" made from steeping substantially equal amounts by volume of:
  powdered saw palmetto;
  powdered horsetail;
  powdered fenugreek seed;
  powdered ginger;
  powdered stinging nettles;
said "tea" optionally further comprising at least one selection from the group consisting of:
  powdered horny goat weed;
  powdered pueraria lobate;
  powdered *Tribulus terrestris;*
  powdered ashwagandha;
  powdered capsicum;
  powdered habenero;
  powdered green tea;
  powdered sage;
  powdered gingko biloba;
  powdered myrrh;
  powdered alpha-hydroxy;
  powdered *Aloe vera;*
  powdered folic acid;
  powdered casein;
  powdered keratin;
  powdered biotin;
  powdered ginseng Root;
  powdered vetiver grass;
  powdered caffeine;
  powdered Co-enzyme Q;
  powdered folate;
  powdered gotukola leaf;
  powdered milk thistle;
  powdered African pygeum;
  powdered niacinamide (NAD) and/or niacin;
  powdered *Nigella sativa;*
  powdered *Eclipta alba;*
  powdered *Centella asiatica;*
  powdered *Phyllanthus emblica;*
  powdered turmeric;
  powdered curcumin; and
  powdered pine bark;
in water, or an oil, (possibly heated up to 190 Degree F.) There are available small colanders produced for use with tea leaves, which work well for producing said "tea". Or one can just add hot water to the mixture of powders. In use a volume of said liquid "tea" applied to a hair challenged area of a human male scalp is the same as the volume of any other Step d) selection. In the alternative, an amount of a mixture of selected powdered materials can be directly applied to a wet scalp.

Another method of encouraging hair growth in male humans, comprising the steps of:

in either order practicing steps a) and b):
- a) providing a human scalp comprising at least one hair challenged area in need of hair regrowth;
- b) providing a multiple electromagnetic radiation source containing helmet or cap suitable for placement adjacent to at least said at least one hair challenged area of said human scalp, and liquid sources of minoxidil, mint oil, and castor bean oil, jojoba oil, melaleuca oil, and providing and applying at least one selection from the group consisting of:
  powdered saw palmetto;
  powdered horsetail;
  powdered fenugreek seed;
  powdered horny goat weed;
  powdered pueraria lobate;
  powdered *Tribulus terrestris;*
  powdered ashwagandha;
  powdered capsicum;
  powdered habenero;
  powdered green tea;
  powdered sage;
  powdered ginger;
  powdered stinging nettles;
  powdered gingko biloba;
  powdered myrrh;
  powdered alpha-hydroxy;
  powdered *Aloe vera;*
  powdered wheat protein;
  powdered wheat starch;
  powdered casein;
  powdered keratin;
  powdered folic acid;
  powdered biotin;
  powdered zinc;
  powdered ginseng Root;
  powdered vetiver grass;
  powdered caffeine;
  powdered Co-enzyme Q;
  powdered folate;
  powdered gotukola leaf;
  powdered milk thistle;
  powdered African pygeum;
  powdered niacinamide (NAD) and/or niacin;
  powdered *Nigella sativa;*
  powdered *Eclipta alba;*
  powdered *Centella asiatica;*
  powdered *Phyllanthus emblica;*
  powdered turmeric;
  powdered curcumin; and
  powdered pine bark;
  wherein when more than one selection is made a mixture of said selections is arrived at by providing, by weight, equal amounts of each selection exact percentages of said powdered selections being limited only in that they sum to 100% in total;
- c) shampooing said scalp, along with any hair present, of said human male;
- d) while the scalp and any hair present are still wet, providing and applying approximately equal amounts of minoxidil from a 5% solution thereof, mint oil, ginger oil, lavender oil, cumin oil and castor oil, each of the later being from a substantially 100% source thereof;
- e) when the scalp and any hair present are substantially dry applying said at least one selection from the group consisting of:
  powdered saw palmetto;
  powdered horsetail;
  powdered fenugreek seed;
  powdered horny goat weed;
  powdered pueraria lobate;
  powdered *Tribulus terrestris;*
  powdered ashwagandha;
  powdered capsicum;
  powdered habenero;
  powdered green tea;
  powdered sage;
  powdered ginger;
  powdered stinging nettles;
  powdered gingko biloba;
  powdered myrrh;
  powdered alpha-hydroxy;
  powdered *Aloe vera;*
  powdered wheat protein;
  powdered wheat starch;
  powdered casein;
  powdered keratin;
  powdered folic acid;
  powdered biotin;
  powdered zinc;
  powdered ginseng Root;
  powdered vetiver grass;
  powdered caffeine;
  powdered Co-enzyme Q;
  powdered folate;
  powdered gotukola leaf;
  powdered milk thistle;
  powdered African pygeum;
  powdered niacinamide (NAD) and/or niacin;
  powdered *Nigella sativa;*
  powdered *Eclipta alba;*
  powdered *Centella asiatica;*
  powdered *Phyllanthus emblica;*
  powdered turmeric;
  powdered curcumin; and
  powdered pine bark;
  wherein when more than one selection is made a mixture of said selections is arrived at by providing, by weight, approximately equal amounts of each selection exact percentages of said powdered selections being limited only in that they sum to 100% in total;
  and not removing applied materials in steps d) and e);
  said method further comprising:
- f) applying electromagnetic radiation provided by said multiple electromagnetic radiation source containing helmet or cap for at least one-half hour to said at least one hair challenged area while at least one of the multiple electromagnetic radiation sources are energized.

Said method can, at some point after step b), involve using said vibrator to apply vibrations to said at least one hair challenged area for at least five minutes.

Said method can provide that the step d) selections further include a volume of liquid comprising a "tea" made from steeping substantially equal amounts by volume of:

powdered saw palmetto;
powdered horsetail;
powdered fenugreek seed;
powdered ginger;
powdered stinging nettles;
said "tea" optionally further comprising at least one selection from the group consisting of:
powdered horny goat weed;
powdered pueraria lobate;
powdered *Tribulus terrestris;*
powdered ashwagandha;
powdered capsicum;
powdered habenero;
powdered green tea;
powdered sage;
powdered gingko biloba;
powdered myrrh;
powdered alpha-hydroxy;
powdered *Aloe vera;*
powdered casein;
powdered keratin;
powdered folic acid;
powdered biotin;
powdered ginseng Root;
powdered vetiver grass;
powdered caffeine;
powdered Co-enzyme Q;
powdered folate;
powdered gotukola leaf;
powdered milk thistle;
powdered African pygeum;
powdered niacinamide (NAD) and/or niacin;
powdered *Nigella sativa;*
powdered *Eclipta alba;*
powdered *Centella asiatica;*
powdered *Phyllanthus emblica;*
powdered turmeric;
powdered curcumin; and
powdered pine bark;
in water, or an oil, (possibly heated to upwards of 190 degrees F.). The "tea" can also contain alcohol in a ratio of about 20:1.
There are available small colanders produced for use with tea leaves, which work well for producing said "tea", or one can just apply hot (eg. 190 degrees Fahrenheit) to the mixture of powders. In use a volume of said liquid "tea" applied to a hair challenged area of a human male scalp is the same as the volume of any other Step d) selection.

It is noted that measurements of "equal amounts" of, for instance minoxidil solution, mint oil (eg. essential peppermint), ginger oil, lavender oil, cumin oil and castor oil can be made with as simple a measuring system as a teaspoon. By simply estimating what constitutes half a teaspoon full for each of the components one can get good enough measurements. And where selection(s) from the group consisting of powdered horny goat weed; powdered pueraria lobate; powdered *Tribulus terrestris*; powdered ashwagandha; powdered capsicum; powdered habenero; powdered green tea; powdered sage; powdered ginger; powdered stinging nettles; powdered gingko biloba; powdered myrrh; powdered alpha-hydroxy; powdered *Aloe vera*; powdered wheat protein; powdered wheat starch; powdered casein; powdered keratin, powdered folic acid and powdered biotin are utilized is/are made, and which multiple selections are made, mixed together and considered as a unit, again the teaspoon volume approach can be applied. In practice Inventor Welch has used an approach of simply pouring approximately amounts of each component into a jar and mixing them, then pouring about a teaspoon full into his cupped left hand and applying it to his hair challenged scalp area. That is to say, "exact" equivalence of amounts is, of course, not required in practice of the methodology, and the Claims should be understood to reflect said basic reality.

Also, the terminology Casein is to be taken to possibly include amino-acids and proteins, especially those common in hair, (eg. Cysteine, Cystine, Arginine, Methionine, Tyrosine, Taurine, Phenylalanine etc.) as well as proteins per se.

Further, wherein said minoxidil from a 5% source thereof, said mint oil, ginger oil, lavender oil, cumin oil and said castor oil from substantially 100% sources thereof are all present in equal amounts by volume, and in which said powdered horny goat weed; powdered pueraria lobate; powdered *Tribulus terrestris*; powdered ashwagandha; powdered capsicum; powdered habenero; powdered green tea; powdered sage; powdered ginger; powdered stinging nettles; powdered gingko biloba; powdered myrrh; powdered alpha-hydroxy; powdered *Aloe vera*; powdered wheat protein; powdered wheat starch; powdered casein; powdered keratin, powdered folic acid and powdered biotin are all present in equal amounts by weight.

It is also noted that in addition to the topical applications described above, practitioners of the methodology herein can also take oral supplements such as selected from the group of:
Saw Palmetto;
Horsetail;
Folic acid;
Biotin;
Multi-vitamins; and
Niacin.

Inventor Welch mentions that of all the possible powdered selections, he has found approximately equal amount of powdered Horsetail, powdered Saw Palmetto, powdered Stinging Nettles, powdered Casein, powdered Ginger and powdered Keratin are best for encouraging hair growth at the rearward portion of his scalp. And when applied to a dry scalp the mixture makes existing hair appear more-full. Further, the powdered Ginger seems more effective in frontal areas of hair challenged regions of his scalp.

It is probably to give a specific example of how to prepare liquids and powders for application in the present invention methodology. For instance, if a user decides to apply minoxidil from a 5% solution thereof, as well as castor oil and peppermint oil, he can measure out a half teaspoon of each and mix them together to form a volume of mixture. Then suppose the user decides to also apply powdered Horsetail, powdered Saw Palmetto, powdered Stinging Nettles, powdered Casein, powdered Ginger and powdered Keratin. He can measure out approximately equal amounts of each by weight, and mix them together. Then a volume of said mixture of said powdered approximately equal to that of the liquids is measure out. In practice the user can apply both the volume of liquid and volume of powdered choices together, or can apply the volume of liquid and then apply the volume of powdered choices once the liquid has substantially dried. The later approach will tend to make existing hair look more-full. And if the methodology is practiced more than once between shampooing, then the next application of liquid will tend to dissolve the powdered selections and perhaps enhance their absorption into the hair challenged portion of the scalp. In interpreting Claims language this example should be kept in mind.

(It is noted that Shampoos are available on the Internet (Ebay) which are variously infused with Biotin and with Ginger and Saw Palmetto etc. A mixture of such shampoos is advised).

Inventor Welch believes that when applying the LED/Laser produced electromagnetic radiation via a cap or helmet, one should orient it so that it primarily affects the rearward portion of the upper scalp. In his experience it is not as effective on forward areas.

Finally in this section, it is to be appreciated that it is important to protect one's eyes against the LED/laser light, mint oil and the other liquids and powders.

Forward Portion of Scalp

While the foregoing methodology is still basically applicable, in the inventor's experience getting hair regrowth results on the forward portion of the human male scalp is a far more difficult problem than in rearward regions. In particular, as previously alluded too, the inventor has noticed that application of electromagnetic radiation is not as successful when applied to the frontal area of his scalp, and that application of vibrations from a vibrator show possibly more success. Further, use of ginger oil and/or powdered ginger seems to be more successful in the frontal areas of the inventor's scalp than other selections. Therefore, the methodology might be amended to emphasize application of pure ginger oil or powdered ginger to the frontal regions of hair challenged regions of a human male scalp.

In the foregoing, Casein should be comprised of not only protein, but of Amino Acids, in particular Arginine and Cystein.

Where alcohol is added to the "Tea" described above, it is preferably ethyl or isopropyl alcohol, and while nominally present in a ratio of about 20:1 with water, can be present in as high as a 1:1 ratio.

While not investigated, it is noted that application of electric discharge and/or a magnetic field in the region of a human male hair challenged scalp might provide benefit.

Many powdered materials and oils are identified in this Disclosure, however many more exist that are not mentioned. The lack of mention of any powdered material or oil etc. is not to be taken as a determination that others might not be as effective or even more so. Other powdered materials and/or oils might be subject in Continuations of this effort.

Further, application of Transforming Growth Factor (TGF Beta) containing Cream to the forward portion of the Scalp can be beneficial.

It is noted that application of warmth (as judged appropriate by user sensation—perhaps a moist 80-90 degrees Fahrenheit) to a hair challenged region of a human male scalp can also be practiced at any point in the methodology.

Finally, Inventor Welch attests that the results he has achieved are not as good as he would like, particularly in the frontal region of his scalp, but that being said the results achieved have been pretty good and they continue to improve slowly. Welch is 76 and much if his hair on the top of his head was dormant for decades. Being truthful it seems that some roots on the top of his head are not responding, at least not quickly. Hair on the edges of the top portion of his head, however, is responding and that edge is making its way centrally, slowly. Therefore, for best results it is advisable for younger people to get started earlier, before roots of hairs become very much damaged.

I claim:

1. A method of encouraging hair growth in male humans, comprising the steps of:
in either order practicing steps a) and b):
  a) providing a human scalp comprising at least one hair challenged area in need of hair regrowth;
  b) providing a multiple electromagnetic radiation source containing helmet or cap, and a vibrator, each suitable for placement adjacent to at least said at least one hair challenged area of said human scalp, and liquid sources of minoxidil, mint oil, ginger oil, lavender oil, cumin oil, castor bean oil, jojoba oil; melaleuca oil, vitamin E infused oil and biotin infused oil;
in either order, at least once a day practicing steps c) and d):
  c) applying electromagnetic radiation provided by said multiple electromagnetic radiation source containing helmet or cap for at least 5 minutes to said at least one hair challenged area while at least one of the multiple electromagnetic radiation sources are energized;
  d) applying to said at least one hair challenged area, and leaving it in place, a volume of liquid comprising at least one selection from the group consisting of:
    minoxidil solution from a 5% source;
    mint oil from a substantially or exactly 100% source thereof;
    ginger oil from a substantially or exactly 100% source thereof;
    lavender oil from a substantially or exactly 100% source thereof;
    castor bean oil from a substantially or exactly 100% source thereof;
    jojoba oil from a substantially or exactly 100% source thereof;
    melaleuca oil from a substantially pure if not per se. 100% pure source thereof;
    cumin oil from a substantially or exactly 100% source thereof;
    D-alpha tocopherol (vitamin E) infused oil; and
    biotin infused oil;
  exact amounts of each selection being limited only in that they sum to 100% by volume in total; and
at some point after step b) using said vibrator to apply mechanical vibrations to said at least one hair challenged area for at least five minutes.

2. A method as in claim 1, in which the step d) mint oil comprises at least 1% liquid menthol by volume.

3. A method as in claim 1, in which all step d) selections are made and are present in a mixture thereof, all said selections being present in substantially equal, or exactly equal amounts by volume.

4. A method as in claim 1, in which the step d) mint and minoxidil components are selected and are present in substantially equal, or exactly equal amounts by volume.

5. A method as in claim 1, in which the step d) group further comprises at least one selection from the consisting of:
  powdered saw palmetto;
  powdered horsetail;
  powdered fenugreek seed;
  powdered horny goat weed;
  powdered pueraria lobate;
  powdered *Tribulus terrestris;*
  powdered ashwagandha;
  powdered capsicum;

powdered habenero;
powdered green tea;
powdered sage;
powdered ginger;
powdered stinging nettles;
powdered gingko biloba;
powdered myrrh;
powdered alpha-hydroxy;
powdered *Aloe vera;*
powdered wheat protein;
powdered wheat starch;
powdered casein;
powdered keratin;
powdered folic acid;
powdered biotin;
powdered zinc;
powdered ginseng Root;
powdered vetiver grass;
powdered caffeine;
powdered Co-enzyme Q;
powdered folate;
powdered gotukola leaf;
powdered milk thistle;
powdered African pygeum;
powdered niacinamide (NAD) and/or niacin;
powdered *Nigella sativa;*
powdered *Eclipta alba;*
powdered *Centella asiatica;*
powdered *Phyllanthus emblica;*
powdered turmeric;
powdered curcumin; and
powdered pine bark;
wherein when more than one selection is made a mixture of said selections is arrived at by providing, by weight, equal amounts of each selection, exact percentages of said powdered selections being limited only in that they sum to 100% in total;
said single selection or a mixture of said selections being considered as a volume unit on par with present minoxidil, peppermint oil, ginger oil, cumin oil and castor bean oil on a volume basis.

6. A method as in claim 5, in which the step d) components selected in claim 1 are present in substantially equal, or exactly equal amounts by volume, and selections in claim 5 are present in substantially equal, or exactly equal amounts by weight, the total amount of said selections in claim 5 being of a volume equivalent to the volumes of each of the selection in claim 1.

7. A method as in claim 1, in which at least one of the multiple electromagnetic radiation sources provide a wavelength of 650 nm at 5 mw's, and in which step c) is practiced for a time of at least at least 1.0 hour.

8. A method as in claim 1, in which all step d) selections are made and a mixture thereof containing substantially equal, or exactly equal amounts by volume of each is applied to said at least one hair challenged area.

9. A method as in claim 1, in which the step d) selections in claim 1 further include a volume of liquid comprising a "tea" made from substantially equal amounts by volume of:
powdered saw palmetto;
powdered horsetail;
powdered fenugreek seed;
powdered ginger;
powdered stinging nettles;
said "tea" optionally further comprising at least one selection from the group consisting of:
powdered horny goat weed;
powdered pueraria lobate;
powdered *Tribulus terrestris;*
powdered ashwagandha;
powdered capsicum;
powdered habenero;
powdered green tea;
powdered sage;
powdered gingko biloba;
powdered myrrh;
powdered alpha-hydroxy;
powdered *Aloe vera;*
powdered folic acid;
powdered casein;
powdered keratin;
powdered biotin;
powdered ginseng Root;
powdered vetiver grass;
powdered caffeine;
powdered Co-enzyme Q;
powdered folate;
Powdered got kola leaf;
powdered milk thistle;
powdered African pygeum;
powdered niacinamide (NAD) and/or niacin;
powdered *Nigella sativa;*
powdered *Eclipta alba;*
powdered *Centella asiatica;*
powdered *Phyllanthus emblica;*
powdered turmeric;
powdered curcumin; and
powdered pine bark;
in water and alcohol in a ratio of about 20:1.

10. A method as in claim 5, in which all selections are made and are present in substantially equal, or exactly equal amounts by weight, the total amount of said selections in claim 5 being of a volume equivalent to each of the volumes of the selection in claim 1.

11. A method as in claim 1, in which the step d) mixture is applied at least twice a day.

12. A method as in claim 5, in which the step d) mixture is applied at least twice a day.

13. A method as in claim 1, which further comprises a step e) that involves providing access to substantially pure or pure per se., one or more selections from the group consisting of:
powdered saw palmetto;
powdered horsetail;
powdered fenugreek seed;
powdered horny goat weed;
powdered pueraria lobate;
powdered *Tribulus terrestris;*
powdered ashwagandha;
powdered capsicum;
powdered habenero;
powdered green tea;
powdered sage;
powdered ginger;
powdered stinging nettles;
powdered gingko biloba;
powdered myrrh;
powdered alpha-hydroxy;
powdered *Aloe vera;*
powdered wheat protein;
powdered wheat starch;
powdered casein;
powdered keratin;
powdered folic acid;

powdered biotin;
powdered zinc;
powdered ginseng Root;
powdered vetiver grass;
powdered caffeine;
powdered Co-enzyme Q;
powdered folate;
powdered gotukola leaf;
powdered milk thistle;
powdered African pygeum;
powdered niacinamide (NAD) and/or niacin;
powdered *Nigella sativa;*
powdered *Eclipta alba;*
powdered *Centella asiatica;*
powdered *Phyllanthus emblica;*
powdered turmeric;
powdered curcumin; and
powdered pine bark;
wherein when more than one selection is made a mixture of said selections is arrived at by providing, by weight, equal amounts of each selection, exact percentages of said powdered selections being limited only in that they sum to 100% in total;
said step e) being:
e) applying to said hair challenged area, after the liquid in step d) has substantially dried, said single selected powder or mixture of selected powders to said at least one region of hair challenged scalp and leaving it in place.

14. A method as in claim 13 which further comprises:
practicing steps f) and g) in either order:
  f) applying electromagnetic radiation provided by a multiple electromagnetic radiation source containing helmet or cap for at least 5 minutes to said at least one hair challenged area while at least one of the multiple electromagnetic radiation sources are energized;
  g) applying to said at least one hair challenged area, and leaving it in place, a liquid mixture comprising, by volume, at least one selection from the group consisting of:
    minoxidil solution from a 5% source;
    mint oil from a substantially pure if not per se. 100% pure source thereof;
    ginger oil from a substantially pure if not per se. 100% pure source thereof;
    lavender oil from a substantially or exactly 100% source thereof;
    castor bean oil from a substantially pure if not per se. 100% pure source thereof;
    jojoba oil from a substantially or exactly 100% source thereof;
    melaleuca oil from a substantially pure if not per se. 100% pure source thereof;
    cumin oil from a substantially pure if not per se. 100% pure source thereof;
    D-alpha tocopherol (vitamin E) infused oil; and
    biotin infused oil;
  exact amounts being limited only in that they sum to 100% by volume.

15. A method as in claim 14, in which the step g) mint oil comprises at least 1% liquid menthol by volume.

16. A method as in claim 14, in which the components in step g) are present in substantially equal, or exactly equal amounts by volume.

17. A method as in claim 14 in which at least one of the multiple electromagnetic radiation sources provide a wavelength of 650 nm at 5 mw's and step f) is practiced for a time selected from the group consisting of:
at least 0.5 hours;
at least 1.0 hours;
at least 1.5 hours; and
at least 2.0 hours.

18. A method of encouraging hair growth in male humans, comprising the steps of:
in either order practicing steps a) and b):
  a) providing a human scalp comprising at least one hair challenged area in need of hair regrowth;
  b) providing a multiple electromagnetic radiation source containing helmet or cap suitable for placement adjacent to at least said at least one hair challenged area of said human scalp and liquid sources of minoxidil, essential peppermint oil, ginger oil, lavender oil, D-alpha tocopherol (vitamin E) infused oil, biotin infused oil, cumin oil and castor bean oil; jojoba oil, melaleuca oil, and of a "tea" prepared from substantially equal amounts of:
    powdered saw palmetto;
    powdered horsetail;
    powdered fenugreek seed;
    powdered ginger;
    powdered stinging nettles;
  said "tea" optionally further comprising at least one selection from the group consisting of:
    powdered horny goat weed;
    powdered pueraria lobate;
    powdered *Tribulus terrestris;*
    powdered ashwagandha;
    powdered capsicum;
    powdered habenero;
    powdered green tea;
    powdered sage;
    powdered gingko biloba;
    powdered myrrh;
    powdered alpha-hydroxy;
    powdered *Aloe vera;*
    powdered folic acid;
    powdered casein;
    powdered keratin;
    powdered biotin;
    powdered ginseng Root;
    powdered vetiver grass;
    powdered caffeine;
    powdered Co-enzyme Q;
    powdered folate;
    powdered gotukola leaf;
    powdered milk thistle;
    powdered African pygeum;
    powdered niacinamide (NAD) and/or niacin;
    powdered *Nigella sativa;*
    powdered *Eclipta alba;*
    powdered *Centella asiatica;*
    powdered *Phyllanthus emblica;*
    powdered turmeric;
    powdered curcumin; and
    powdered pine bark;
  wherein when more than one selection is made a mixture of said selections is arrived at by providing, by weight, equal amounts of each selection exact percentages of said powdered selections being limited only in that they sum to 100% by volume;
  c) shampooing said scalp, along with any hair present, of a human male;

d) while the scalp and any hair present are still wet, providing and applying approximately equal amounts of minoxidil from a 5% solution thereof, mint oil, ginger oil, lavender oil, cumin oil, castor oil, vitamin E infused oil and biotin infused oil, each of the later being from a substantially 100% source thereof, and of said "tea"; and e) when the scalp and any hair present are substantially dry applying said at least one selection from the group consisting of:
   powdered saw palmetto;
   powdered horsetail;
   powdered ginger;
   powdered stinging nettles;
   powdered casein;
   powdered keratin;
said mixture optionally further comprising at least one selection from the group consisting of:
   essential peppermint oil;
   ginger oil;
   lavender oil;
   vitamin E infused oil;
   biotin infused oil;
   cumin oil
   castor oil;
   jojoba oil;
   melaleuca oil;
   cumin oil;
   D-alpha tocopherol (vitamin E) infused oil;
   biotin infused oil;
   powdered fenugreek seed;
   powdered horny goat weed;
   powdered pueraria lobate;
   powdered *Tribulus terrestris;*
   powdered ashwagandha;
   powdered capsicum;
   powdered habenero;
   powdered green tea;
   powdered sage;
   powdered gingko biloba;
   powdered myrrh;
   powdered alpha-hydroxy;
   powdered *Aloe vera;*
   powdered folic acid;
   powdered biotin;
   powdered ginseng Root;
   powdered vetiver grass;
   powdered caffeine;
   powdered Co-enzyme Q;
   powdered folate;
   powdered gotukola leaf;
   powdered milk thistle;
   powdered African pygeum;
   powdered niacinamide (NAD) and/or niacin;
   powdered *Nigella sativa;*
   powdered *Eclipta alba;*
   powdered *Centella asiatica;*
   powdered *Phyllanthus emblica;*
   powdered turmeric;
   powdered curcumin; and
   powdered pine bark.
wherein when more than one selection is made a mixture of said selections is arrived at by providing, by weight, equal amounts of each selection exact percentages of said powdered selections being limited only in that they sum to 100% in total;
and not removing applied materials in steps d) and e);
said method further comprising:
   f) applying electromagnetic radiation provided by said multiple electromagnetic radiation source containing helmet or cap for at least one-half hour to said at least one hair challenged area while at least one of the multiple electromagnetic radiation sources are energized.

19. A method as in claim 1, which, prior to step b) comprises shampooing scalp and any hair present, and while wet providing and applying approximately equal amounts of minoxidil from a 5% solution thereof, and essential peppermint oil, ginger oil, lavender oil, vitamin E infused oil, biotin infused oil, cumin oil and castor oil; and of a "tea" prepared from substantially equal amounts of:
   powdered saw palmetto;
   powdered horsetail;
   powdered fenugreek seed;
   powdered ginger;
   powdered stinging nettles;
said "tea" optionally further comprising at least one selection from the group consisting of:
   powdered horny goat weed;
   powdered pueraria lobate;
   powdered *Tribulus terrestris;*
   powdered ashwagandha;
   powdered capsicum;
   powdered habenero;
   powdered green tea;
   powdered sage;
   powdered gingko biloba;
   powdered myrrh;
   powdered alpha-hydroxy;
   powdered *Aloe vera;*
   powdered folic acid;
   powdered casein;
   powdered keratin;
   powdered biotin;
   powdered ginseng Root;
   powdered vetiver grass;
   powdered caffeine;
   powdered Co-enzyme Q;
   powdered folate;
   powdered gotukola leaf;
   powdered milk thistle;
   powdered African pygeum;
   powdered niacinamide (NAD) and/or niacin;
   powdered *Nigella sativa;*
   powdered *Eclipta alba;*
   powdered *Centella asiatica;*
   powdered *Phyllanthus emblica;*
   powdered turmeric;
   powdered curcumin; and
   powdered pine bark;
in water and alcohol in a ratio of about 20:1.

20. A method as in claim 1, which prior to step b) comprises shampooing scalp and any hair present, and while wet providing and applying approximately equal amounts of minoxidil from a 5% solution thereof, and essential peppermint oil from a substantially 100% or exactly 100% source thereof, as well as a mixture of substantially or exactly equal amounts of:
   powdered saw palmetto;
   powdered horsetail;
   powdered ginger;
   powdered stinging nettles;
   powdered casein;
   powdered keratin;

said mixture optionally further comprising at least one selection from the group consisting of:
  essential peppermint oil;
  ginger oil;
  lavender oil;
  vitamin E infused oil;
  biotin infused oil;
  cumin oil
  castor oil;
  jojoba oil;
  melaleuca oil;
  cumin oil;
  D-alpha tocopherol (vitamin E) infused oil;
  biotin infused oil;
  powdered fenugreek seed;
  powdered horny goat weed;
  powdered pueraria lobate;
  powdered *Tribulus terrestris*;
  powdered ashwagandha;
  powdered capsicum;
  powdered habenero;
  powdered green tea;
  powdered sage;
  powdered gingko biloba;
  powdered myrrh;
  powdered alpha-hydroxy;
  powdered *Aloe vera*;
  powdered folic acid;
  powdered biotin;
  powdered ginseng Root;
  powdered vetiver grass;
  powdered caffeine;
  powdered Co-enzyme Q;
  powdered folate;
  powdered gotukola leaf;
  powdered milk thistle;
  powdered African pygeum;
  powdered niacinamide (NAD) and/or niacin;
  powdered *Nigella sativa*;
  powdered *Eclipta alba*;
  powdered *Centella asiatica*;
  powdered *Phyllanthus emblica*;
  powdered turmeric;
  powdered curcumin; and
  powdered pine bark.

\* \* \* \* \*